US011192841B2

(12) United States Patent
Myers et al.

(10) Patent No.: US 11,192,841 B2
(45) Date of Patent: Dec. 7, 2021

(54) PROCESSES FOR PREPARING HALOGENATED ALKANES

(71) Applicant: Blue Cube IP LLC, Clayton, MO (US)

(72) Inventors: John D. Myers, Clayton, MO (US); Max Tirtowidjojo, Clayton, MO (US)

(73) Assignee: Blue Cube IP LLC, Clayton, MO (US)

( * ) Notice: Subject to any disclaimer, the term of this patent is extended or adjusted under 35 U.S.C. 154(b) by 0 days.

(21) Appl. No.: 16/981,977

(22) PCT Filed: Apr. 2, 2019

(86) PCT No.: PCT/US2019/025332
§ 371 (c)(1),
(2) Date: Sep. 17, 2020

(87) PCT Pub. No.: WO2019/195247
PCT Pub. Date: Oct. 10, 2019

(65) Prior Publication Data
US 2021/0107849 A1    Apr. 15, 2021

Related U.S. Application Data

(60) Provisional application No. 62/652,033, filed on Apr. 3, 2018.

(51) Int. Cl.
| | | |
|---|---|---|
| *C07C 17/275* | (2006.01) | |
| *B01J 19/00* | (2006.01) | |
| *B01J 19/18* | (2006.01) | |
| *B01J 23/72* | (2006.01) | |
| *B01J 23/745* | (2006.01) | |
| *B01J 31/18* | (2006.01) | |
| *C07C 19/041* | (2006.01) | |

(52) U.S. Cl.
CPC .......... *C07C 17/275* (2013.01); *B01J 19/0066* (2013.01); *B01J 19/1818* (2013.01); *B01J 23/72* (2013.01); *B01J 23/745* (2013.01); *B01J 31/185* (2013.01); *B01J 2219/00051* (2013.01); *B01J 2219/00162* (2013.01); *C07C 19/041* (2013.01)

(58) Field of Classification Search
CPC ..... C07C 17/275; C07C 19/041; C07C 19/01; B01J 23/72; B01J 23/745; B01J 31/185
See application file for complete search history.

(56) References Cited

U.S. PATENT DOCUMENTS

| | | |
|---|---|---|
| 6,313,360 B1 | 11/2001 | Wilson et al. |
| 8,907,147 B2 | 12/2014 | Wang et al. |
| 2016/0107956 A1* | 4/2016 | Ondrus .................. C07C 17/04 570/181 |

OTHER PUBLICATIONS

International Search Report dated Jun. 24, 2019, PCT/US2019/025332.
Written Opinion of the International Searching Authority dated Jun. 24, 2019, PCT/US2019/025332.

* cited by examiner

*Primary Examiner* — Jafar F Parsa
(74) *Attorney, Agent, or Firm* — Polsinelli PC

(57) ABSTRACT

The present invention provides improved processes for preparing halogenated alkanes. The processes comprise reacting an alkene, a halogenated alkene, or combinations thereof and a halogenated methane with at least one chlorine atom, while using an absorption device.

32 Claims, No Drawings

PROCESSES FOR PREPARING HALOGENATED ALKANES

CROSS-REFERENCE TO RELATED APPLICATIONS

This application is a national stage entry of PCT/US2019/025332 filed Apr. 2, 2019, which claims the benefit of U.S. Provisional application 62/652,033 filed Apr. 3, 2018, each of said applications are expressly incorporated herein by reference in their entirety.

FIELD OF THE INVENTION

The present disclosure generally relates to processes for preparing halogenated alkanes.

BACKGROUND OF THE INVENTION

Halogenated alkanes are useful intermediates for many products including agricultural products, pharmaceuticals, cleaning solvents, solvents, gums, silicones, and refrigerants. The processes to prepare halogenated alkanes can be time consuming, moderately efficient, and lack reproducibility.

One widely known method for preparing halogenated alkanes is through a telomerization process. This process comprises contacting a halogenated methane comprising at least one chlorine atom and an alkene or halogenated alkene in the presence of a catalyst. Even though these telomerization processes are useful, these processes have variable yields, low reproducibility, large amounts of waste, and high unit manufacturing costs.

One subset of highly sought after halogenated alkanes are chlorinated propanes, especially 1,1,1,3-tetrachloropropane and 1,1,1,3,3-pentachloropropane, which are useful intermediates for many products, including refrigerants and agricultural products. A general process for their preparation consists of reacting an alkene or a halogenated alkene, carbon tetrachloride, a trialkylphosphate, and an iron catalyst in a telomerization process. U.S. Pat. No. 4,650,914 teaches such a process where the process is conducted in batch mode, using a non-powder form of an iron and mechanical stirring. U.S. Pat. Nos. 6,313,360 and 8,907,147 disclose a continuous process using powdered iron and mechanical stirring. In these processes, the telomerization reaction occurs in the liquid phase. The alkene or halogenated alkene is introduced into the liquid phase, the headspace above the reaction mixture, or both, then the alkene or halogenated alkene must be absorbed into the liquid phase of the reaction mixture. Since the alkene or halogenated alkene has a partial solubility in carbon tetrachloride, the alkene or halogenated alkene is used in excess to maintain the concentration of the alkene or halogenated alkene in the liquid phase. At the end of the process, the unreacted alkene or halogenated alkene is normally purged as waste or vented to the atmosphere.

Since the concentration of the alkene or halogenated alkene in the liquid phase is dependent on the absorption of the alkene or halogenated alkene in the liquid phase, many of the processes have reduced kinetics and reduced rates. Various methods have been employed to maintain or increase the concentration or absorption of the alkene or halogenated alkene in the liquid phase, thus maintaining the kinetic and rates of these processes. Other methods are employed to limit the amount of the alkene or halogenated alkene leaving the process as waste. Some of these methods comprise compressing and recirculating the alkene from the headspace to the bottom of the reactor, utilizing special mechanical devices to increase the absorption of the alkene or halogenated alkene in carbon tetrachloride, such as gas inducing impellers, and expensive alkene or halogenated alkene recycling equipment. Even though these methods require the use of expensive mechanical equipment, a large portion of the alkene or halogenated alkene is still purged to waste. Thus, these processes can be moderately efficient yet lack reproducibility, lack consistent yields, utilize various alkene recovery systems, use numerous scrubbers, have large waste factors, and provide the chlorinated propane at a higher unit manufacturing cost.

Developing a process which can prepare halogenated alkanes, and chlorinated propanes where the process would exhibit high reproducible, consistent higher yields, greater through-put, improved recycle strategies, reduced manufacturing cost, and reduced amounts of waste is desirable.

SUMMARY OF THE INVENTION

Provided herein are processes for preparing and isolating halogenated alkanes via the reaction between an alkene, a halogenated alkene, or combinations thereof and a halogenated methane comprising at least one chlorine atom. The process comprising: a. forming a reaction mixture in a reactor by contacting: a liquid phase comprising a halogenated methane comprising at least one chlorine atom, at least one ligand; and at least one catalyst comprising a metal, metal salt, or combinations thereof; an alkene, halogenated alkene, or combinations thereof; wherein the alkene, halogenated alkene, or combinations thereof and is at least partially absorbed into the liquid phase; b. optionally heating, stirring or both heating and stirring the reaction mixture; and c. producing halogenated alkanes and heavy by-products. One skilled in the art would appreciate that stirring the reaction mixture and heating the reaction mixture may occur one before the other or at the same time, which is true throughout this application. The process further comprises an absorption device comprising a packed column, a tray column, or combinations thereof. A liquid distributor is optionally used in combination with the absorption device. The liquid feed to the absorption device comprises a fresh liquid feed, a recycle liquid feed comprising a fresh liquid feed, a recycle liquid feed from the reactor, a recycle feed from the absorber, or combinations thereof. As the liquid phase of the reaction mixture is circulated through the absorption device under process conditions detailed below, the absorption device provides an increased concentration of the alkene, halogenated alkene, or combinations thereof in the liquid phase.

Other features and iterations of the invention are described in more detail below.

DETAILED DESCRIPTION OF THE INVENTION

Disclosed herein are processes for the preparation of halogenated alkanes. In general, the process comprises a reaction between an alkene, halogenated alkene, or combinations thereof and halogenated methane comprising at least one chlorine atom under conditions detailed below.

In all embodiments, the absorption device comprises a packed column, a tray column, or combinations thereof. An eductor, a nozzle, or combinations thereof may be used in combination with the absorption device. The reaction mixture is contacted with the absorption device wherein the alkene, halogenated alkene, or combinations thereof is at least partially absorbed into the liquid phase. This absorption device provides increased interaction of an alkene, halogenated alkene, or combinations thereof with the liquid phase. Thus, the absorption device provides an increased concentration of the alkene, halogenated alkene, or combinations thereof in the liquid phase of the reaction mixture. In one embodiment, the absorption device is located inside the reactor above the reaction mixture having a liquid phase. In a further aspect, the liquid phase contains a metal containing and/or metallic catalyst. In an alternate embodiment, the absorption device is located outside the reactor.

These processes have been shown to be an improvement in yield, purity, cycle time, selectivity, reduction of waste, lower unit manufacturing cost, and through-put as compared to other conventional methods. In an additional aspect of the present invention, at least a portion of the separated reactants are recycled back into the process to provide added efficiency and cost reduction of the process.

(I) Processes for Preparing Halogenated Alkanes

One aspect of the present disclosure encompasses processes for the preparation of halogenated alkanes. The processes comprise forming a liquid phase reaction mixture comprising a halogenated methane comprising at least one chlorine atom, an alkene, halogenated alkene, or combinations thereof, at least one ligand, and at least one catalyst. Once this reaction mixture is formed, stirring the reaction mixture and heating the reaction mixture may occur one before the other or at the same time, and then the liquid phase is contacted with an absorption device. The absorption device increases the concentration of the alkene, halogenated alkene, or combinations thereof in the liquid phase, which maintains or increases the kinetics of the process. The output from the process comprises the halogenated alkanes and heavy by-products.

(a) Reaction Mixture

The processes commence by preparing a reaction mixture comprising a halogenated methane comprising at least one chlorine atom, an alkene, halogenated alkene, or combinations thereof, at least one ligand, and at least one catalyst.

(i) Alkene, Halogenated Alkene, or Combinations Thereof

A wide variety of alkenes, halogenated alkenes, or combinations thereof may be used in the process. As appreciated by the skilled artisan, the alkene, halogenated alkene, or combinations thereof may be introduced in the reaction as a liquid or a gas, wherein the alkene, halogenated alkene, or combinations thereof may be at least partially soluble in the liquid phase and may have an affinity for the absorption material. In various embodiments, the alkene, halogenated alkene, or combinations thereof may be introduced above the surface of the liquid phase or below the surface of the liquid phase through a port in the reactor. Under conditions of the process as detailed below, the alkene, halogenated alkene, or combinations thereof may be liquid and then may undergo a phase transition from a liquid to a gas. As appreciated by the skilled artisan, the pressure in the reactor may be maintained by adding the alkene, halogenated alkene, or combination thereof.

Generally, the alkene, halogenated alkene, or combinations thereof comprise between 2 and 5 carbon atoms. Non-limiting examples of alkenes may be ethylene, propylene, 1-butene, 2-butene, isobutene, 1-pentene, 2-pentene, 3-pentene, 2-methyl-2-butene, 2-methyl-1-butene, and 3-methyl-1-butene. Non-limiting examples of halogenated alkenes may be vinyl chloride, vinyl bromide, vinyl fluoride, allyl chloride, allyl fluoride, 1-chloro-2-butene, 1-fluoro-2 butene, 3-chloro-1-butene, 3-fluoro-1-butene, 3-chloro-1-pentene, 3-fluoro-1-pentene, and combinations thereof. In one embodiment, the alkene comprises ethylene, propylene, 1-butene, 2-butene, isobutylene, or combinations thereof. Still more preferably, the alkene comprises ethylene. In another embodiment, the halogenated alkene is vinyl chloride, vinylidene chloride, or combinations thereof. In a different embodiment, the halogenated alkene is vinyl chloride.

(ii) Halogenated Methane Comprising at Least One Chlorine Atom

A wide variety of halogenated methanes comprising at least one chlorine atom may be used in this process. Non-limiting examples of halogenated methane comprising at least one chlorine atom include methyl chloride, methylene chloride, chloroform, carbon tetrachloride, chlorofluoromethane, dichloromonofluoromethane, trichlorofluoromethane, difluorochloromethane, trifluorochloromethane, bromochloromethane, dibromochloromethane, tribromochloromethane, chloroiodomethane, chlorodiiodomethane, chlorotriiodomethane, bromochlorofluoromethane, bromochlorodifluoromethane, chlorodibromofluoromethane, bromochlorofluoroiodomethane, bromochlorodiiodomethane, and combinations thereof. In an embodiment, the halogenated methane comprising at least one chlorine atom is carbon tetrachloride.

In general, the halogenated methane comprising at least one chlorine atom may be used in excess. Generally, the molar ratio of the halogenated methane comprising at least one chlorine atom to an alkene, a halogenated alkene, or combinations thereof may range from 0.1:1 to about 100:1. In various embodiments, the molar ratio of the halogenated methane comprising at least one chlorine atom to an alkene, a halogenated alkene, or combinations thereof may range from 0.1:1 to about 100:1, from 0.5:1 to about 75:1, from 1:1 to about 10:1, or from 1.2:1 to about 5:1. In various embodiments, the molar ratio of the halogenated methane comprising at least one chlorine atom to an alkene, a halogenated alkene, or combinations thereof may range from 1.2:1 to about 2:1. The halogenated methane comprising at least one chlorine atom and an alkene, a halogenated alkene, or combinations thereof are essentially dry, i.e., it has a water content of the below 1000 ppm. Lower water concentrations are preferred, but not required.

Ligand

In various embodiments, a ligand may be used in the process. The ligand, as the skilled artisan appreciates, may form a complex with the catalyst, with the resulting complex soluble in the reaction media.

In one embodiment, the ligand is a phosphorus containing compound. Examples of phosphorus containing compound may include trialkylphosphates, trialkylphosphites, or combinations thereof. Suitable non-limiting examples of trialkylphosphates and trialkylphosphite may include triethylphosphate, tripropylphosphate, triisopropylphosphate, tributylphosphate, trimethylphosphite, triethylphosphite, tripropylphosphite, triisopropylphosphite, tributylphosphite, and tri-tertbutylphosphite. In one preferred embodiment, the phosphorus containing compound is a trialkylphosphate, such as tributylphosphate.

(iv) Catalyst

A wide variety of catalysts may be used in the process. In some embodiments, the catalyst is a transition metal catalyst. As used herein, the term "transition metal catalyst" refers to a transition metal in the zero oxidation state, i.e., the elemental metal, a transition metal containing alloy, a transition metal salt, or combinations thereof. Transition metals useful in the processes described herein include all transition metals. In one embodiment, the at least one catalyst comprises iron metal, copper metal, iron containing compound, copper containing compound, iron containing alloy, copper containing alloy, or combinations thereof. In one embodiment, iron and copper metal are preferred. Acceptable transition metal containing alloys include gilding metal, bronze, magnesium bronze, tin bronze, aluminum bronze, phosphor bronze, red brass, brass, cast iron, pig iron, steel, tool steel, and wootz steel.

The transition metal or transition metal containing alloy may be in the form of a foil, a sheet, a screen, a wool, a wire, a ball, a plate, a pipe, a rod, a bar or a powder; while powders are not preferred, they are acceptable. In various embodiments, the transition metal catalyst may be immobilized on the surface of a support. Non-limiting examples of suitable supports may be alumina, silica, silica gel, diatomaceous earth, carbon and clay. Specific examples of supported catalysts include copper on alumina, copper on silica, iron on carbon, iron on diatomaceous earth, and iron on clay. In an embodiment, the transition metal catalyst may be elemental iron, elemental copper, a copper alloy, an iron alloy, or combinations thereof.

Generally, the surface area of the metal may range from 1 $cm^2/(kg/hr)$ to about 10,000 $cm^2/(kg/hr)$. In various embodiments, the surface area of the metal may range 1 $cm^2/(kg/hr)$ to about 10,000 $cm^2/(kg/hr)$, from about 100 $cm^2/(kg/hr)$ to about 7,500 $cm^2/(kg/hr)$, from about 1,000 $cm^2/(kg/hr)$ to about 5,000 $cm^2/(kg/hr)$, or from 2,000 $cm^2/(kg/hr)$ to about 4,000 $cm^2/(kg/hr)$. In one preferred embodiment, the surface area of the metal is 100 to 2500 $cm^2/(kg/hr)$. In another preferred embodiment, the surface area of the metal is or 1750 to 2250 $cm^2/(kg/hr)$. In still another embodiment, the surface area of the metal is 75-425 $cm^2/(kg/hr)$ or 100-350 $cm^2/(kg/hr)$.

In an embodiment, the at least one catalyst may comprise a transition metal salt. Non-limiting examples of suitable transition metal salts may include acetates, acetyacetonates, alkoxides, butyrates, carbonyls, dioxides, halides, hexonates, hydrides, mesylates, octanoates, nitrates, nitrosyl halides, nitrosyl nitrates, sulfates, sulfides, sulfonates, phosphates, and combinations thereof. Examples of suitable transition metal salts include copper (I) chloride, copper (II) chloride, copper (I) bromide, copper (I) iodide, iron (II) chloride, iron (III) chloride, iron (II) bromide, iron (II) iodide, iron (III) bromide, copper (II) oxide, and iron (III) oxide. In an embodiment, the transition metal salt may be copper (I) chloride, copper (II) chloride, iron (II) chloride, iron (III) chloride, or combinations thereof.

In one embodiment, the transition metal catalyst is an iron catalyst comprising iron in various oxidation states, such as Fe(0), Fe(II), and Fe(III). In one aspect, the iron catalyst may be Fe(0) alone as elemental iron or an iron alloy. In an additional aspect, the iron catalyst may comprise a mixture of Fe(0) and Fe(II) salt. In another aspect, the iron catalyst may comprise a mixture of Fe(0) and Fe(III) salt. In still another aspect, the iron catalyst may comprise a mixture of Fe(II) salt and Fe(III) salt. In yet another aspect, the iron catalyst may comprise a mixture of Fe(0), Fe(II) salt, and Fe(III) salt. In still another embodiment, an electrochemical cell may be utilized to adjust the ratio of Fe(II) and Fe(III) in the reaction. When the ligand is present, it may complex with at least some of the iron metal and/or iron salt present in the reaction.

In another embodiment, the transition metal catalyst is a copper catalyst comprising copper in various oxidation states, such as Cu(0), Cu(I), and Cu(II). In one aspect, the copper catalyst may be Cu(0) alone as elemental copper or a copper alloy. In an additional aspect, the copper catalyst may comprise a mixture of Cu(0) and Cu(I) salt. In another aspect, the copper catalyst may comprise a mixture of Cu(0) and Cu(II) salt. In still another aspect, the copper catalyst may comprise a mixture of Cu(I) salt and Cu(II) salt. In yet another aspect, the copper catalyst may comprise a mixture of Cu(0), Cu(I) salt, and Cu(II) salt. In still another embodiment, an electrochemical cell may be utilized to adjust the ratio of Cu(I) and Cu(II) in the reaction. When the ligand is present, it may complex with at least some of the copper metal and/or copper salt present in the reaction.

In one embodiment, the ligand comprises a trialkylphosphate, trialkylphosphite, or combinations thereof and wherein the ligand is complexed to Fe(II), Fe(III), Cu(I), Cu(II), or combinations thereof. In one preferred embodiment, the ligand is a trialkylphosphate, such as tributylphosphate (TBP).

As appreciated by the skilled artisan, the transition metal catalyst, once in the process, may undergo and oxidation and/or reduction to produce an activated catalytic species in various oxidation states. The oxidation state of these active catalytic species may vary, and may be for examples (I), (II), and (III). In one aspect, the active iron catalyst may in the Fe(I) oxidation state. In another aspect, the active iron catalyst may be Fe(II). In still another aspect, the active iron catalyst may be in the Fe(III) oxidation state. In an additional aspect, the active iron catalyst may comprise a mixture of Fe(I) and Fe(II). In still another aspect, the active iron catalyst may comprise a mixture of Fe(I) and Fe(III) oxidation states. In yet another aspect, the active iron catalyst may be in the Fe(II) and Fe(III) oxidation states. In another aspect, the active iron catalyst may in the Fe(I), Fe(II) and Fe(III) oxidation states. The oxidation state of these active copper catalytic species may vary, and may be for examples (I) and (II). In one aspect, the active copper catalyst may in the Cu(I) oxidation state. In another aspect, the active copper catalyst may be Cu(II). In an additional aspect, the active copper catalyst may comprise a mixture of Cu(I) and Cu(II).

Generally, the molar ratio of the at least one dissolved catalyst to halogenated methane comprising at least one chlorine atom may range from about 0:1 to about 0.1:1. In various embodiments, the molar ratio of the at least one dissolved catalyst to halogenated methane comprising at least one chlorine atom may range from 0:1 to about 0.1:1, from 0.0001:1 to about 0.05:1, or preferably from 0.0025:1 to about 0.01:1.

In general, the molar ratio of the dissolved elemental metal to the ligand may range from 1:1 to about 1:1000. In various embodiments, the molar ratio of the dissolved elemental metal to the ligand may range from 1:1 to about 1:1000, from 1:1 to about 1:500, from 1:1 to about 1:100, or from 1:1 to about 1:10. In one preferred embodiment, the molar ratio of the dissolved elemental metal to the ligand may range from about 1:1.5 to about 1:3.

Generally, the molar ratio of the metal salt to the ligand may range from 1:1 to about 1:1000. In various embodiments, the molar ratio of the metal salt to the phosphorus containing compound may range from 1:1 to about 1:1000, from 1:1 to about 1:500, from 1:1 to about 1:100, or from 1:1 to about 1:10. In one preferred embodiment, the molar ratio of the metal salt to the phosphorus containing compound may range from about 1:1.5 to about 1:3.

In another embodiment, the at least one catalyst in a continuous reactor may be part of a fixed bed of metal as a source of catalyst. In still another embodiment, the at least one fixed bed metallic catalyst source in a continuous reactor may be part of a cartridge. In still another embodiment, the at least one fixed bed metallic catalyst source may be part of a structured or un-structured packing where the at least one fixed bed metallic catalyst source is a part of the packing or un-structured packing. Using a fixed bed, a cartridge, structured packing, or unstructured packing, the metallic catalyst source may be contained and easily replaced.

(v) Introduction of the Catalyst(s) into the Process

Generally, the at least one catalyst may be introduced to the process in various ways. In one aspect, the at least one catalyst comprising a metal, a metal alloy, a metal salt(s), or combinations thereof may be introduced directly into the process. In another aspect, a catalyst solution comprising at least one catalyst may be prepared by dissolving at least a portion of the metal, a metal alloy, metal salt(s), or combinations thereof in a mixture of halogenated methane comprising at least one chlorine atom and the ligand, then adding this solution to the reactor. In yet another embodiment, a catalyst solution may be generated inside the reactor by mixing the metal, a metal alloy, metal salt(s), or combinations thereof, the ligand, and the halogenated methane comprising at least one chlorine atom. As appreciated by the skilled artisan, other methods for introducing the at least one catalyst or solution of the at least one catalyst into the reactor may be envisioned. The alkene may be in the reactor before the catalyst is added, the alkene may be added to the reactor after the catalyst, or at the same time.

(b) Absorption Device

In all embodiments, the alkene, halogenated alkene, or combinations thereof is absorbed into the liquid phase by circulating the liquid phase and the alkene, halogenated alkene, or combinations thereof, through the absorption device. The absorption device provides increased interaction between the alkene, halogenated alkene, or combinations thereof and the liquid phase of the reaction mixture or a fresh liquid feed. In all embodiments, the absorption device comprises a packed column, a tray column, or combinations thereof. A liquid distributor is optionally used in combination with the absorption device.

A liquid distributor is a device used to distribute the liquid(s) before they enter the absorption device, which results in the even wetting of the packing material. Typically, the liquid leaving the liquid distributor has a lower velocity than the liquid entering the liquid distributor. Liquid distributors are known in the art and include nozzles, e.g., pig tail nozzles, sprayers, perforated pipes and any other device that spreads a stream of liquid. Liquid distributors convert a stream of liquid into a shower, spray or mist. In one preferred embodiment, the liquid distributor is located above the absorption device. The shower, spray or mist leaving the liquid distributor then coats the top of the absorption device and evenly wets the packing in the absorption device.

As the process commences, the liquid phase from the reaction mixture is pumped and circulated through the packed column, tray column, or combinations thereof, where the column provides increased gas-liquid phase interaction and achieves essentially complete absorption of the alkene, halogenated alkene, or combinations thereof, into the liquid phase of the reaction mixture. Common tray types include sieve trays, bubble cap trays and valve trays. As the process continues, one or more fresh material feeds comprising the at least one halogenated methane comprising at least one chlorine atom, the alkene, halogenated alkene, or combinations thereof, the ligand, and the at least one catalyst comprising a metal, a metal alloy, a metal salt(s), or combinations thereof or combinations of any and all of the above are introduced to the reactor/are introduced into the process. The resulting combination of the liquid phase from the reaction mixture and fresh material feeds allows for increased absorption of the alkene, halogenated alkene, or combinations thereof into the total liquid phase comprising the reaction mixture and fresh liquid feeds. The packings for the packed or tray column may be in the form of a structured or unstructured packing. Non-limiting examples of structured packing may be Flexipac®, Flexipac HC®, Intalox® saddles, Pall rings, Raschig rings, Berl saddles, splined rings, Sulzer®, wire gauze structured packing, or combinations thereof. These structured packing may in various sizes, configurations, and corrugation sizes. Non-limiting examples of corrugation sizes may be extruded, perforated and waffled, perforated and grooved, perforated, smooth, and combinations thereof. Non-limiting examples of unstructured packing may be Flexiring®, Hy-Pak®, IMTP®, Intalox®, Ultra®, or combinations thereof. These unstructured packing may be in various sizes and configurations.

In various embodiments, an eductor may be used in combination with the absorption device. As appreciated by the skilled artisan, even though there is essentially complete absorption of the alkene, halogenated alkene, or combinations thereof, in the packing of the absorption device, a portion of the alkene, halogenated alkene, or combinations thereof is desorbed from the liquid phase of the reaction mixture and accumulates in the headspace above the liquid phase of the reaction mixture. In order to increase the concentration of the alkene, halogenated alkene, or combinations thereof in the liquid phase, an eductor may be employed. An eductor withdraws a portion of the liquid phase of the reaction mixture from the reactor and pumps the liquid phase back into the reactor through at least one gas educting nozzle. The eductor nozzle provides suction in the eductor which pulls a portion of the alkene, halogenated alkene, or combinations thereof from the headspace above the liquid phase of the reaction mixture, mixes the alkene, halogenated alkene, or combinations thereof with the circulated liquid phase, and returns the resulting mixture of liquid and the alkene, halogenated alkene, or combinations thereof back into the liquid phase of the reactor, where the liquid has increased absorption of the gas, when compared to the circulated liquid phase.

In other embodiments, a nozzle may be used in combination with the absorption device. As appreciated by the skilled artisan, a portion of the liquid phase is withdrawn from the reaction mixture from the reactor and is pumped through the nozzle creating droplets of the liquid phase into the gas phase causing increased absorption of the alkene, halogenated alkene, or combinations thereof. The resulting mixture of liquid and gas goes back into the liquid phase of the reactor, where the liquid has increased absorption of the alkene, halogenated alkene, or combinations thereof, as compared to the circulated liquid phase.

In various embodiments, the absorption device may be inside the reactor, outside the reactor, or combinations thereof. The absorption device may be part of the reactor, part of a column, or a separate device.

Generally, when the absorption device is located within the reactor, the absorbing device is located above the liquid phase of the reaction mixture. In operation, the alkene, halogenated alkene, or combinations thereof flows into the absorption device. The liquid phase from the reactor is pumped to the top of the absorption device flowing downwards through the absorption device. The liquid phase contacts the absorption device where the alkene, halogenated alkene, or combinations thereof has increased interaction with the liquid phase from the reaction mixture. The liquid phase returns to the reactor where the liquid has increased concentration of the alkene, halogenated alkene, or combinations thereof, as compared to the circulated liquid phase.

In another embodiment, the absorption device is located in a separate chamber from the reactor. In this configuration, the liquid phase of the reaction mixture contacts the absorption device, providing an increased amount of absorption of the alkene, halogenated alkene, or combinations thereof into the liquid phase of the reaction mixture.

In another embodiment, the absorption device may be connected to the fixed bed, cartridge, structured packing, or unstructured packing comprising at least one catalyst. In this configuration, the liquid phase of the reaction mixture contacts the absorption device, providing an increased amount of the alkene, halogenated alkene, or combinations thereof into the liquid phase of the reaction mixture. This liquid phase of the reaction mixture then contacts the at least one catalyst in the fixed bed, cartridge, structured packing, or unstructured packing thus producing the halogenated alkane and heavy by-products under reaction conditions as described below. In an alternate configuration, the liquid phase of the reaction mixture contacts the at least one catalyst in the fixed bed, cartridge, structured packing, or unstructured packing providing a suitable concentration of at least one catalyst in solution. This liquid phase then contacts the absorption device, providing the alkene, halogenated alkene, or combinations thereof into the liquid phase at an increased concentration. The output from this configuration produces the halogenated alkane and heavy by-products under reaction conditions as described below.

(c) Reaction Conditions

As appreciated by the skilled artisan, the above process may be run in a batch mode or a continuous mode, with continuous mode preferred.

In a continuous mode, a stirred tank reactor may be used, or a series of stirred tank reactor to approach the performance of an ideal plug flow reactors may be utilized to improve the overall efficiency of the process. In another embodiment, the process in continuous modes may be stirred in various methods to improve the mixing of the gas-liquid system as appreciated by the skilled artisan.

Mixing of the contents within the reactor is necessary to provide turbulence within the reactor and flow through the absorption device. This flow through the absorption device provides interaction of the alkene, halogenated alkene, or combination thereof with the liquid phase of the reaction mixture thereby maintaining the kinetic of the process.

As appreciated by the skilled artisan, there are many methods to adequately stir the process and also provide an adequate flow through the absorption device. In various embodiments, the liquid phase of the reaction mixture in the reactor may be stirred utilizing jet mixing using at least one nozzle. In other embodiments, jet mixing utilizing at least one eductor may be utilized. In still other embodiments, jet mixing utilizing at least one nozzle and at least one eductor may be utilized. In yet another embodiment, mechanical stirring may be used. In still another embodiment, a combination of all the above methods of stirring may be used.

Jet mixing utilizing at least one nozzle, as appreciated by the skilled artisan, withdraws a portion of the liquid phase of the reaction mixture from the reactor and pumps the liquid phase back into the reactor through at least one nozzle, thereby creating turbulence in the liquid phase and increased flow through the absorption device. The at least one nozzle may be positioned below the surface of the liquid phase, thereby creating turbulence in the liquid phase and providing increased mixing. The at least one nozzle may be positioned at the surface of the liquid phase or directed through the gas phase into the liquid phase, thereby providing increased turbulence of the reaction mixture but also provides increased absorption of the gas phase into the liquid phase.

Jet mixing utilizing at least one eductor, as appreciated by the skilled artisan, withdraws a portion of the liquid phase of the reaction mixture from the reactor and pumps the liquid phase back into the reactor through at least one gas educting nozzle. The eductor nozzle provides suction in the eductor which pulls gas from the gas phase of the reaction mixture, mixes the gas with the circulated liquid phase, and returns the resulting mixture of liquid and gas back into the liquid phase of the reactor where the liquid has increased absorption of the gas, as compared to the circulated liquid phase. When the flow from the eductor nozzle is directed towards the liquid phase of the reaction mixture, increased absorption of the gas into the liquid phase, increased turbulence of the reaction mixture, and increased flow through the absorption device results.

Jet mixing may also utilize at least one nozzle and at least one eductor. In this configuration, as described above, not only are increased turbulence in the reaction mixture and increased flow through the absorption device achieved, but increased gas absorption of the gas into the liquid phase is realized.

In other embodiments, a draft tube may be utilized in the process. The draft tube provides an internal recirculation of the reaction mixture. The circulation may be induced by energy from the at least one liquid jets, from the at least one gas educting nozzle, from rising gas bubbles within the reactor, or a combination thereof.

As appreciated by the skilled artisan, at least one of the above described methods or a combination of these may be utilized in the process. In a preferred embodiment, jet mixing using at least one eductor nozzle, wherein the flow from the eductor nozzle is directed towards the liquid phase of the reaction mixture is utilized.

In general, the process for the preparation of halogenated alkanes will be conducted to maintain the temperature from about 80° C. to about 140° C. using an internal or external heat exchanger. As appreciated by the skilled artisan, the temperature of the reactor is partially maintained by boiling off or vaporizing a portion of the reactants and products. In various embodiments, the temperature of the reaction may be maintained from about 80° C. to about 140° C., from 85°

C. to about 130° C., from 90° C. to about 120° C., or from about 95° C. to about 115° C.

Generally, the process may be conducted at a pressure of about atmospheric pressure (~14.7 psi, 101.3 kPa) to about 200 psi (1379 kPa) so the amount of the gases and liquid are in suitable quantities so the reaction may proceed and maintain the kinetics of the process. In various embodiments, the pressure of the process may be from about atmospheric pressure (~14.7 psi) to about 200 psi, from about 20 psi to about 180 psi, from about 40 psi to about 160 psi, from about 80 psi to about 140 psi, or from 100 psi to about 120 psi.

Generally, the reaction is allowed to proceed for a sufficient period of time until the reaction is complete, as determined by any method known to one skilled in the art, such as chromatography (e.g., GC-gas chromatography). The duration of the reaction may range from about 5 minutes to about 16 hours. In some embodiments, the duration of the reaction may range from about 5 minutes to about 16 hours, from about 1 hour to about 12 hours, from about 2 hours to about 10 hours, from about 4 hours to about 8 hours, or from about 5 hours to about 7 hours.

(d) Output from the Process to Prepare Halogenated Alkanes

The process, as outlined above, produces the halogenated alkane, light by-products, and heavy by-products. In general, the process produces the halogenated alkanes in at least 50 weight percent (wt %) in the liquid phase of the reaction mixture. In various embodiments, the halogenated alkane is produced in at least 50 wt %, in at least 60 wt %, in at least 70 wt %, in at least 80 wt %, in at least 90 wt %, in at least 95 wt %, or in at least 99 wt % in the liquid phase of the reaction mixture.

The heavy by-products are produced in less than 5 weight % in the entire product distribution. In various embodiments, these heavy impurities may be less than 4 weight %, less than 3 weight %, less than 2 weight %, or less than 1 weight %.

In preferred embodiments, the halogenated alkane is a chloroalkane. In an embodiment, the chloroalkane is 1,1,1,3-tetrachloropropane. In another embodiment, the chloroalkane is 1,1,1,3,3,-pentachloropropane. In yet another embodiment, the chloroalkane is 1,1,1,3,3,3-hexachloropropane is formed.

In one embodiment, the halogenated alkane is further reacted with a chlorinating agent, a transition metal catalyst, a base, or combinations thereof to prepare other chlorinated propanes or chlorinated propenes.

(II) Separation of the Halogenated Alkane and Recycle Streams

The next step in the process comprises separating purified halogenated alkane from the contents of the reaction mixture comprising halogenated alkane, a halogenated methane comprising at least one chlorine atom, an alkene, halogenated alkene, or combinations thereof, the ligand, at least one catalyst, heavy by-products, and light by-products through at least one of the first separator and a second separators in order to isolate the halogenated alkane in the desired yield and/or purity. In various embodiments, the at least one of the first separator and the second separator may a distillation column or a multistage distillation column. Additionally, the at least one of the first separator and the second separator may further comprise a reboiler, a bottom stage, or a combination thereof. Various distillation columns may be used in this capacity. In one embodiment, a side draw column or a distillation column which provides outlet stream from an intermediate stage or a divided wall column (dividing wall column (DWC)) is a single shell, fully thermally coupled distillation column capable of separating mixtures of three or more components into high purity products may be used as a separator. Upon separation from the reaction mixture, various product effluent streams are produced comprising halogenated alkane, a halogenated methane comprising at least one chlorine atom, an alkene, halogenated alkene, or combinations thereof, the ligand, heavy by-products, light by-products, or combinations thereof. A portion of various product effluent streams produced by the process may be recycled back into the reactor, via a recycle liquid feed, to provide increased kinetics, increased efficiencies, reduced overall cost of the process, increased selectivity of the desired halogenated alkane, and increased yield of the desired halogenated alkane.

As appreciated by the skilled artisan, separating the purified halogenated alkane from the reaction mixture of the reactor would produce at least two product effluent streams. In various embodiments, separating the purified chlorinated alkane may produce three, four, or more product effluent streams depending on the separation device utilized. As an example, the separation of the halogenated alkane from the contents of the reactor using two product effluent streams is shown below.

The process utilizing one separator commences by transferring a portion of the reaction mixture or the reaction mixture into the separator. In this operation, a portion of the reaction mixture may be separated into two distinct product effluent streams, product effluent stream (a) and (b). Product effluent stream (a) comprising the halogenated alkane, halogenated methane comprising at least one chlorine atom, and an alkene, halogenated alkene, or combinations thereof is separated from product effluent stream (b) which comprises the heavy by-products, the ligand, and at least one catalyst.

In an embodiment, a solid/liquid phase separation device may be utilized. During the heating of the process, solids are formed. Utilization of this solid/liquid separation device removes the solids and prevents fowling of the reactor.

In another embodiment, a portion of product effluent stream (a) may be transferred into a second separator, producing two additional product effluent streams (c) and (d). Product effluent stream (c) comprises a halogenated methane comprising at least one chlorine atom and the alkene, halogenated alkene, or combinations thereof while product effluent stream (d) comprises the halogenated alkane. Product effluent stream (d) may be further transferred into additional separators to achieve the desired yield and/or purity of the halogenated alkane.

In another embodiment, the first and second separation devices may be contained in a single separation device. In this configuration, a portion of the reaction mixture or the reaction mixture into a separator. In this operation, a portion of the reaction mixture may be separated into three distinct product effluent streams, product effluent stream (e), (f), and (g). Product effluent stream (f) comprising the halogenated alkane may be removed as a side stream, product effluent stream (e) comprising unconverted halogenated methane with at least one chlorine atom, the alkene, halogenated alkene, or combinations thereof, and light byproducts may be removed as the overhead stream, and product effluent stream (g) comprising the ligand and heavy by-products may be removed as a bottom stream. This configuration would provide additional efficiency as compared to the other configurations. Each product effluent streams (b), (c), (e) and/or (g) may be returned to the reactor (i.e., recycled), purified, or purged, in whole or in part. In yet another embodiment, the first column may use a dividing wall column to improve the purification of the product. Thus, at least a portion of the reaction mixture from the reactor is treated to remove the light components and the heavy components from the halogenated alkane. The light and/or heavy components are optionally recycled to the reactor. Or, at least a portion of the reaction mixture from the reactor is treated to remove heavy components, catalysts, ligands, or combinations thereof, wherein the product effluent stream comprising heavy components, catalysts, ligands, or combinations thereof are recycled to the reactor.

In various embodiments, at least a portion of product effluent streams (b) and/or (g) may be recycled back into the reactor. These streams may also be fed into another process to produce other products. In yet another embodiment, product effluent stream (b) and/or (g) may be separated so that a portion of the heavy byproducts are returned to the reactor while the remaining portion of the heavy byproducts may be purged from the reactor. These various product effluent streams may also be fed into another process to produce other products. These steps may be performed in order to improve the efficiency, reduce the cost, reduce contaminants, and increase through-put of the process.

In another embodiment, at least a portion of product effluent streams (b), (c), (e) and/or (g) may be mixed with fresh material feeds comprising the at least one halogenated methane comprising at least one chlorine atom, the alkene, halogenated alkene, or combinations thereof, the ligand, and the at least one catalyst comprising a metal, a metal salt(s), or combinations thereof or combinations of any and all of the above, before being recycled back into the reactor, via a recycle liquid feed, in batch mode or continuous mode. To be clear, the recycle liquid feed may contain metallic catalyst. In various embodiments, the recycle product effluent streams and fresh materials feeds may be introduced into the reactor separately or mixed together before entering the process. The introduction of these fresh material feeds into the reactor or mixing the recycle product effluent streams with fresh material feeds increases the efficiency of the process, reduces the overall cost, maintains the kinetics, increase the through-put, and reduces the by-products produced by the process. The amounts of the recycled product effluent streams to the reactor or fresh material feeds added to the reactor may be the same or different. One way to measure the amount of recycled product effluent streams and/or fresh material feeds being added to the reactor is to identify the mass flow of each of these materials. The recycled product effluent streams to the reactor has a product effluent streams mass flow, while the fresh material feeds being added to the reactor has a fresh material feed mass flow. Mass flows may be measured using methods known in the art.

Generally, the mass of the product effluent stream mass flow being recycled to the fresh material feed mass flow is adjusted to maintain the conversion of the process and the kinetics of the process.

In yet another embodiment, the at least one catalyst may be separated from the reaction mixture by means of extraction. This extraction, using water or another polar solvent, may remove spent or deactivated catalyst. In another embodiment, the extraction may separate the active transition metal ligand complex which may be introduced back into the reactor or other downstream processes. Using the extraction processes defined above may provide added efficiency to the process in respect to overall cost.

Product effluent streams (a), (d), or (f) comprising the halogenated alkane produced in the process typically have a yield of at least about 20%. In various embodiments, the product effluent streams (a) or (d) comprising halogenated alkane produced in the process may have a yield of at least about 30%, at least about 50%, at least about 70%, at least about 75%, at least about 80%, at least about 85%, at least about 90%, at least about 95%, or at least about 99%.

The halogenated alkane contained in product effluent streams (a), (d), or (f) from the process may have a weight percent at least about 50%, at least about 60%, at least about 65%, at least about 70%, at least about 75%, at least about 80%, at least about 85%, at least about 90%, at least about 95%, at least about 99%, at least about 99.5%, or at least about 99.9%.

(III) Preferred Embodiments: 1,1,1,3-Tetrachloropropane (a) Process for the Preparation of 1,1,1,3-tetrachloropropane One aspect of the present disclosure encompasses processes for the preparation of 1,1,1,3-tetrachloropropane. The process commences by contacting ethylene, carbon tetrachloride, a phosphorus containing compound comprising trialkylphosphate, trialkylphosphite, or combinations thereof, and at least one catalyst under the reaction conditions described above. In one embodiment, the phosphorus containing compound is a trialkylphosphate such as tributylphosphate.

(b) Absorption Device

The absorption device is described above in Section (I)(b).

(c) Reaction Conditions

The stirring of the reaction mixture is described above in Section (I)(c).

(d) Output from the Process to Prepare 1,1,1,3-Tetrachloropropane

In a preferred embodiment, the process produces 1,1,1,3-tetrachloropropane and also heavy by-products with boiling point higher than that of the desired product 1113 and other impurities such as light byproducts with boiling point less than that of the desired product 1113. As appreciated by the skilled artisan, the process is conducted to minimize the formation of byproducts and maximize the formation of 1,1,1,3-tetrachloropropane. Non-limiting examples of the heavy by-products may include 1,1,1,5-tetrachloropentane and pentachloropropane isomers.

Generally, the process produces 1,1,1,3-tetrachloropropane in at least 50 wt % yield, and produces heavy by-product impurities in less than 5 weight % in the entire product distribution. In various embodiments, the 1,1,1,3-tetrachloropropane is produced in at least 50 wt %, in at least 60 wt %, in at least 70 wt %, in at least 80 wt %, in at least 90 wt %, in at least 95 wt %, or in at least 99 wt % in the liquid phase of the reactor. In other embodiments, the heavy by-products may be less than 4 weight %, less than 3 weight %, less than 2 weight %, or less than 1 weight % in the liquid phase of the reactor.

(e) Separation of 1,1,1,3-Tetrachloropropane and Recycle Streams

The separation of 1,1,1,3-tetrachloropropane and the recycle product effluent streams is described above in Section (I)(e).

Product effluent streams (a), (d), or (f) comprising the 1,1,1,3-tetrachloropropane produced in the process may have a yield of at least about 20%. In various embodiments, the product effluent streams (a), (d), and/or (f), comprising 1,1,1,3-tetrachloropropane produced in the process, may have a yield of at least about 30%, at least about 50%, at least about 70%, at least about 75%, at least about 80%, at least about 85%, at least about 90%, at least about 95%, or at least about 99%.

The 1,1,1,3-tetrachloropropane contained in product effluent streams (a), (d), and/or (f) from the process may have a weight percent at least about 50%, at least about 60%, at least about 65%, at least about 70%, at least about 75%, at least about 80%, at least about 85%, at least about 90%, at least about 95%, at least about 99%, at least about 99.5%, or at least about 99.9%.

(IV) Process for the Preparation of 1,1,1,3,3-Pentachloropropane

(a) Process for the Preparation of 1,1,1,3,3-pentachloropropane

One aspect of the present disclosure encompasses processes for the preparation of 1,1,1,3,3-pentachloropropane. The process commences by contacting vinyl chloride, carbon tetrachloride, a phosphorus containing compound comprising trialkylphosphate, trialkylphosphite, or combinations thereof, and at least one catalyst, under the reaction conditions described above. In one embodiment, the phosphorus containing compound is a trialkylphosphate such as tributylphosphate.

(b) Absorption Device

The absorption device is described above in Section (I)(b).

(c) Reaction Conditions

The stirring of the reaction mixture is described above in Section (I)(c).

(d) Output from the Process to Prepare 1,1,1,3,3-Pentachloropropane

In a preferred embodiment, the process produces 1,1,1,3,3-pentachloropropane and also heavy by-products with boiling point higher than that of the desired product 1,1,1,3,3-pentachloropropane and other impurities such as light byproducts with boiling point less than that of the desired product 1,1,1,3,3-pentachloropropane. As appreciated by the skilled artisan, the process is conducted to minimize the formation of byproducts and maximize the formation of 1,1,1,3,3-pentachloropropane. Non-limiting examples of the heavy by-products include hexachloropropane isomers.

Generally, the process produces 1,1,1,3,3-pentachloropropane in at least a 50 wt % and produces heavy by-product impurities in less than 5 weight % in the entire product distribution. In various embodiments, the 1,1,1,3,3-pentachloropropane is produced in at least 50 wt %, in at least 60 wt %, in at least 70 wt %, in at least 80 wt %, in at least 90 wt %, in at least 95 wt %, or in at least 99 wt % in the liquid phase of the reactor. In other embodiments, the heavy by-products may be less than 4 weight %, less than 3 weight %, less than 2 weight %, or less than 1 weight % in the liquid phase of the reactor.

(e) Separation of 1,1,1,3,3-Pentachloropropane and Recycle Streams

The separation of 1,1,1,3,3-pentachloropropane and the recycle streams is described above in Section (I)(e).

Product effluent streams (a), (d), and/or (f) comprising the 1,1,1,3,3-pentachloropropane produced in the process may have a yield of at least about 20%. In various embodiments, the product effluent streams (a), (d), and/or (f) comprising 1,1,1,3,3-pentachloropropane produced in the process may have a yield of at least about 30%, at least about 50%, at least about 70%, at least about 75%, at least about 80%, at least about 85%, at least about 90%, at least about 95%, or at least about 99%.

The 1,1,1,3,3-pentachloropropane contained in product effluent streams (a), (d), and/or (f) from the process may have a weight percent at least about 50%, at least about 60%, at least about 65%, at least about 70%, at least about 75%, at least about 80%, at least about 85%, at least about 90%, at least about 95%, at least about 99%, at least about 99.5%, or at least about 99.9%.

(V) Process for the Preparation of 1,1,1,3,3,3-Hexachloropropane

(a) Process for the Preparation of 1,1,1,3,3,3-hexachloropropane

One aspect of the present disclosure encompasses processes for the preparation of 1,1,1,3,3,3-hexachloropropane. The process commences by contacting vinylidene chloride, carbon tetrachloride, a phosphorus containing compound comprising trialkylphosphate, trialkylphosphite, or combinations thereof, and at least one catalyst, under the reaction conditions described above. In one embodiment, the phosphorus containing compound is a trialkylphosphate such as tributylphosphate.

(b) Absorption Device

The absorption device is described above in Section (I)(b).

(c) Reaction Conditions

The stirring of the reaction mixture is described above in Section (I)(c).

(d) Output from the Process to Prepare 1,1,1,3,3,3-Hexachloropropane

In a preferred embodiment, the process produces 1,1,1,3,3-pentachloropropane and also heavy by-products with boiling point higher than that of the desired product 1,1,1,3,3,3-hexachloropropane and other impurities such as light byproducts with boiling point less than that of the desired product 1,1,1,3,3,3-hexachloropropane. As appreciated by the skilled artisan, the process is conducted to minimize the formation of byproducts and maximize the formation of 1,1,1,3,3,3-hexachloropropane.

Generally, the process produces 1,1,1,3,3,3-hexachloropropane in at least a 50 wt % and produces heavy by-product impurities in less than 5 weight % in the entire product distribution. In various embodiments, the 1,1,1,3,3,3-hexachloropropane is produced in at least 50 wt %, in at least 60 wt %, in at least 70 wt %, in at least 80 wt %, in at least 90 wt %, in at least 95 wt %, or in at least 99 wt % in the liquid phase of the reactor. In other embodiments, the heavy by-products may be less than 4 weight %, less than 3 weight %, less than 2 weight %, or less than 1 weight % in the liquid phase of the reactor.

(e) Separation of 1,1,1,3,3,3-Hexachloropropane and Recycle Streams

The separation of 1,1,1,3,3,3-hexachloropropane and the recycle streams is described above in Section (I)(e).

Product effluent streams (a), (d), and/or (f) comprising the 1,1,1,3,3,3-hexachloropropane produced in the process may have a yield of at least about 20%. In various embodiments, the product effluent streams (a), (d), and/or (f) comprising 1,1,1,3,3,3-hexachloropropane produced in the process may have a yield of at least about 30%, at least about 50%, at least about 70%, at least about 75%, at least about 80%, at least about 85%, at least about 90%, at least about 95%, or at least about 99%. The 1,1,1,3,3,3-hexachloropropane contained in product effluent streams (a), (d), and/or (f) from the process may have a weight percent at least about 50%, at least about 60%, at least about 65%, at least about 70%, at least about 75%, at least about 80%, at least about 85%, at least about 90%, at least about 95%, at least about 99%, at least about 99.5%, or at least about 99.9%.

(VI) Further Reaction of the Halogenated Alkanes

In one aspect, disclosed herein are processes for the conversion of halogenated alkanes, such as 1,1,1,3-tetrachloropropane, 1,1,1,3,3-pentachloropropane, or 1,1,1,3,3,3-hexachloropropane to one or more hydrofluoroolefins. These processes comprise contacting the halogenated alkanes in additional dehydrohalogenation/halogenation reactions or contacting the halogenated alkane with a fluorinating agent in the presence of a fluorination catalyst in a single or two or more reaction. These processes can be conducted in either gas phase or liquid phase with the gas phase being preferred at temperatures ranging from 50° C. to 400° C.

Generally, a wide variety of fluorinating agents can be used. Non-limiting examples of fluorinating agents include HF, $F_2$, ClF, $AlF_3$, KF, NaF, $SbF_3$, $SbF_5$, $SF_4$, or combinations thereof. The skilled artisan can readily determine the appropriate fluorination agent and catalyst. Examples of hydrofluoroolefins that may be produced utilizing these processes include, but are not limited to 2,3,3,3-tetrafluoroprop-1-ene (HFO-1234yf), 1,3,3,3-tetrafluoroprop-1-ene (HFO-1234ze), 3,3,3-trifluoroprop-1-ene (HFO-1243zf), and 1-chloro-3,3,3-trifluoroprop-1-ene (HFCO-1233zd).

DEFINITIONS

When introducing elements of the embodiments described herein, the articles "a", "an", "the" and "said" are intended to mean that there are one or more of the elements. The terms "comprising", "including" and "having" are intended to be inclusive and mean that there may be additional elements other than the listed elements.

The term "250FB" or "1113" refers to 1,1,1,3-tetrachloropropane.

The term "240FA" or "11133" refers to 1,1,1,3,3-pentachloropropane.

The term "111333" refers to 1,1,1,3,3,3-hexachloropropane.

The term "Tet" refers to carbon tetrachloride.

The term "TBP" refers to tributylphosphate.

Having described the invention in detail, it will be apparent that modifications and variations are possible without departing from the scope of the invention defined in the appended claims.

EXAMPLES

The following examples illustrate various embodiments of the invention.

Example 1: Preparation of 1,1,1,3-Tetrachloropropane (250fb) using unstructured Packing A 7 L reactor was constructed of Monel. To the bottom was added Fe(0) with a total surface area of 4000 $cm^2$(kg/hr). To the top was added about 3 liters of 0.25-inch Monel Pro-Pak packing. $CCl_4$ containing 1.5 wt % TBP and 0.25 wt % $FeCl_3$ was fed to the reactor to obtain about 4-11 hr residence time and ethylene was fed sufficient to maintain pressure at 100 psig. The temperature was controlled at 110° C. Liquid was circulated from the bottom of the reactor to the top at 200× the fresh feed and liquid was withdraw at a rate to control the level a little above the bed of iron tube section. The conversion of $CCl_4$ was found to vary from 60 to 94% and the selectivity to 250fb was 91 to 96% respectively.

Example 2: Preparation of 1,1,1,3-Tetrachloropropane (250fb) Without Using Structured Packing Example 1 was repeated except that the packing was removed from the headspace of the reactor and replaced with a commercial ½" Schutte and Koerting ½" eductor with a 3.5 mm orifice. While the conversion and selectivity was found to be similar to those found with packing, a significant pumping energy, however, was required to overcome the additional pressure drop of 1.2-4.5 bar the across the eductor nozzle to get the same reactor performance/ yield. This demonstrates the use of packing results in a lower operating cost.

Example 3: Preparation of 1,1,1,3,3-Pentachloropropane (250fa) Without Using Structured Packing Carbon tetrachloride containing 2.5 weight % TBP and $FeCl_3$:TBP mole ratio about 0.5 was fed to an absorber/ reactor system at a rate of 3.1 kg/hr. A liquid circulation flow of 790 kg/h was pumped from the absorber bottom through a heat exchanger and a reactor, then back into the top of the absorber through a ½-inch nozzle. The absorber was 4-inch diameter and 36-inch height and was maintained at about 50% liquid level. The top of the absorber above the liquid level was packed with ¼-inch Pro-Pak Monel packing. The gas phase of the absorber comprised vinyl chloride, which was continuously fed to the absorber to maintain the pressure at 1.5 barg. The temperature of the circulating liquid was maintained at 100° C. The reactor was 4-inch diameter and 36-inch tall, and was packed with ¼-inch carbon steel rings. Liquid was continuously withdrawn from the system to control absorber level. The conversion of carbon tetrachloride in the withdrawn liquid was 70% and the selectivity to the desired 240fa product was 95.6%. The packed section in the absorber was sufficient to achieve mass transfer of vinyl chloride without additional mechanical agitation.

What is claimed is:

1. A process for preparing halogenated alkanes, the process comprising:
   a. in a reactor, forming a reaction mixture having a liquid phase, wherein the reaction mixture comprises: a halogenated methane comprising at least one chlorine atom; an alkene, a halogenated alkene, or combinations thereof; a ligand; and at least one metal, metal alloy, metal salt, or combinations thereof; wherein the alkene, halogenated alkene, or combinations thereof is at least partially absorbed into the liquid phase;
   b. producing at least one halogenated alkane and heavy by-products;
   wherein the alkene, halogenated alkene, or combinations thereof is absorbed into the liquid phase by circulating the liquid phase through an absorption device;
   wherein the absorption device comprises a packed column, a trayed column, or combinations thereof;
   wherein a liquid distributor is optionally used in combination with the absorption device; and
   wherein the liquid feed to the absorption device comprises a fresh liquid feed, a recycle liquid feed comprising a fresh liquid feed, a recycle liquid feed from the reactor, a recycle feed from the absorber, or combinations thereof.

2. The process of claim 1, wherein the absorption device is located inside the reactor above the reaction mixture above the reaction mixture having a liquid phase.

3. The process of claim 1, wherein the absorption device is located outside of the reactor.

4. The process of claim 3, wherein an eductor, a nozzle, a mechanical stirrer, or combinations thereof are used to stir the reaction mixture.

5. The process of claim 1, wherein at least one catalyst comprises iron metal, copper metal, iron containing compound, copper containing compound, iron containing alloy, copper containing alloy, or combinations thereof.

6. The process of claim 1, wherein at least one catalyst comprises Fe(0), Fe(II), Fe(III), or combinations thereof.

7. The process of claim 1, wherein at least one catalyst comprises Cu(0), Cu(I), Cu(II), or combinations thereof.

8. The process of claim 6, wherein the at least one catalyst further comprises a ligand.

9. The process of claim 8, wherein the ligand comprises a trialkylphosphate, trialkylphosphite, or combinations thereof and wherein the ligand is complexed to Fe(II), Cu(I), Cu(II), or combinations thereof.

10. The process of claim 1, wherein the trialkylphosphate comprises triethylphosphate, tripropylphosphate, triisopropylphosphate, tributylphosphate, or combinations thereof.

11. The process of claim 1, wherein the trialkylphosphite comprises trimethylphosphite, triethylphosphite, tripropylphosphite, triisopropylphosphite, tributylphosphite, tri-ter-tbutylphosphite, or combinations thereof.

12. The process of claim 1, wherein the halogenated alkane is a chlorinated alkane.

13. The process of claim 12, wherein the chlorinated alkane comprises 1,1,1,3-tetrachloropropane.

14. The process of claim 12, wherein the chlorinated alkane comprises 1,1,1,3,3-pentachloropropane.

15. The process of claim 12, wherein the chlorinated alkane comprises 1,1,1,3,3,3-hexachloropropane.

16. The process of claim 1, wherein the halogenated methane comprising at least one chlorine atom comprises carbon tetrachloride.

17. The process of claim 1, wherein the alkene comprises ethylene, propylene, 1-butene, 2-butene, isobutylene, or combinations thereof.

18. The process of claim 1, wherein the halogenated alkene comprises vinyl chloride, vinylidene chloride, or combinations thereof.

19. The process of claim 1, wherein the reaction mixture is stirred using jet stirring.

20. The process of claim 19, wherein the reactor comprises at least one nozzle, at least one educting nozzle, or combinations thereof are used in combination with jet stirring.

21. The process of claim 19, wherein the reactor further comprises a draft tube.

22. The process of claim 1, wherein the reaction mixture is maintained at a temperature from about 80° C. to about 140° C.

23. The process of claim 1, wherein the process is conducted at a pressure from about atmospheric pressure (~14.7 psi, 101.3 kPa) to about 200 psi (1379 kPa).

24. The process of claim 1, wherein the process is continuous.

25. The process of claim 1, wherein the weight % of the halogenated alkane is at least 50 weight % in the liquid phase of the reaction mixture.

26. The process of claim 1, wherein the reaction is conducted in a series of stirred tank reactors.

27. The process of claim 1, wherein at least a portion of the reaction mixture from the reactor is treated to remove the light components and heavy components from the halogenated alkane.

28. The process of claim 1, wherein at least a portion of the reaction mixture from the reactor is treated to remove heavy components, catalysts, ligands, or combinations thereof, wherein the product effluent stream comprising heavy components, catalysts, ligands, or combinations thereof are recycled back to the reactor.

29. The process of claim 13, wherein the halogenated alkane is further reacted with a chlorinating agent, a transition metal catalyst, a base, or combinations thereof to prepare other chlorinated propanes or chlorinated propenes.

30. The process of claim 1, wherein fresh material feeds comprising the at least one halogenated methane comprising at least one chlorine atom, the alkene, halogenated alkene, or combinations thereof, the ligand, the at least one catalyst comprising a metal, a metal salt(s), or combinations thereof, or combinations of any and all of the above is added to the reactor.

31. The process of claim 30, wherein the material being recycled to the reactor has a product effluent stream mass flow, while the fresh material feeds being added to the reactor has a fresh material feed mass flow, wherein the mass ratio of the product effluent stream mass flow to the fresh material feed mass flow is adjusted to maintain the conversion of the process and the kinetics of the process.

32. The process of claim 1, wherein the halogenated alkane is converted to a fluorinated product.

* * * * *